US012558063B2

(12) United States Patent
Peterson et al.

(10) Patent No.: US 12,558,063 B2
(45) Date of Patent: *Feb. 24, 2026

(54) TRIPHALANGEAL ULTRASOUND PROBE STABILIZATION FEATURE

(71) Applicant: Bard Access Systems, Inc., Salt Lake City, UT (US)

(72) Inventors: Bart D. Peterson, Farmington, UT (US); Steffan Sowards, Salt Lake City, UT (US); Bradley M. Wilkinson, North Haledon, NJ (US); Anthony K. Misener, Bountiful, UT (US); Mark Newby, Kamas, UT (US); William Robert McLaughlin, Bountiful, UT (US)

(73) Assignee: Bard Access Systems, Inc., Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 18/765,541

(22) Filed: Jul. 8, 2024

(65) Prior Publication Data

US 2024/0358350 A1      Oct. 31, 2024

Related U.S. Application Data

(63) Continuation of application No. 17/871,491, filed on Jul. 22, 2022, now Pat. No. 12,048,586.
(Continued)

(51) Int. Cl.
*A61B 8/00*      (2006.01)
*A61B 17/34*      (2006.01)
(52) U.S. Cl.
CPC ............ *A61B 8/44* (2013.01); *A61B 17/3403* (2013.01)

(58) Field of Classification Search
CPC ........ A61B 8/44; A61B 8/4455; F16M 13/00; F16M 13/04; H04M 1/05; H04M 1/0203
See application file for complete search history.

(56) References Cited

U.S. PATENT DOCUMENTS

| 8,707,549 B2 | 4/2014 | Burns et al. |
| 10,153,800 B2 | 12/2018 | Hirsch |

(Continued)

FOREIGN PATENT DOCUMENTS

| JP | 2016105745 A | 6/2016 |
| KR | 20170037584 A | 4/2017 |

(Continued)

OTHER PUBLICATIONS

Agu, Emmanuel, et al. "The smartphone as a medical device: Assessing enablers, benefits and challenges." 2013 IEEE u International Workshop of Internet-of-Things Networking and Control (IoT-NC). IEEE, 2013.

(Continued)

*Primary Examiner* — Carolyn A Pehlke
(74) *Attorney, Agent, or Firm* — Rutan & Tucker LLP

(57)      ABSTRACT

A triphalangeal stabilization feature for an ultrasound probe includes a stationary member, a manipulation member, and a locking member. The stationary member has a shape conforming to an outer surface of the ultrasound probe. The manipulation member is slidingly coupled to the stationary member and extends away from the stationary member to provide a surface for one or more of a user's fingers. The locking member is configured to prevent movement of the manipulation member with respect to the stationary member at one or more different positions along the stationary member.

11 Claims, 8 Drawing Sheets

Related U.S. Application Data

(60) Provisional application No. 63/235,000, filed on Aug. 19, 2021, provisional application No. 63/225,278, filed on Jul. 23, 2021.

(56)                References Cited

U.S. PATENT DOCUMENTS

| | | |
|---|---|---|
| 2002/0148277 A1 | 10/2002 | Umeda |
| 2003/0060714 A1 | 3/2003 | Henderson et al. |
| 2006/0173331 A1 | 8/2006 | Booton et al. |
| 2008/0146936 A1 | 6/2008 | Furia et al. |
| 2008/0300491 A1* | 12/2008 | Bonde .................. A61B 8/0841 |
| | | 600/461 |
| 2012/0209121 A1 | 8/2012 | Boudier |
| 2015/0038844 A1* | 2/2015 | Blalock ................ A61B 8/4494 |
| | | 600/440 |
| 2016/0213398 A1* | 7/2016 | Liu ....................... A61B 8/0891 |
| 2019/0076121 A1 | 3/2019 | Southard et al. |
| 2020/0015783 A1 | 1/2020 | Sturnick |
| 2020/0349342 A1 | 11/2020 | Ralston et al. |
| 2021/0140580 A1 | 5/2021 | Nahum et al. |
| 2021/0315366 A1* | 10/2021 | Licitra ................... A45C 11/00 |

| | | | |
|---|---|---|---|
| 2022/0183431 A1 | 6/2022 | Chiang et al. |
| 2022/0273262 A1 | 9/2022 | Moore et al. |
| 2023/0023910 A1 | 1/2023 | Peterson et al. |
| 2023/0165569 A1 | 6/2023 | Sonnenschein et al. |

FOREIGN PATENT DOCUMENTS

| | | |
|---|---|---|
| KR | 102106093 B1 | 5/2020 |
| WO | 2020160550 A1 | 8/2020 |
| WO | 2023004133 A1 | 1/2023 |

OTHER PUBLICATIONS

KR Translation of NPL from Examiner.

PCT/US2022/038045 filed Jul. 22, 2022 International Search Report and Written Opinion dated Nov. 7, 2022.

U.S. Appl. No. 17/871,491, filed Jul. 22, 2022 Non-Final Office Action dated Nov. 24, 2023.

U.S. Appl. No. 17/871,491, filed Jul. 22, 2022 Notice of Allowance dated Mar. 20, 2024.

U.S. Appl. No. 17/871,491, filed Jul. 22, 2022 Restriction Requirement dated Sep. 7, 2023.

* cited by examiner

TRIPHALANGEAL ULTRASOUND PROBE STABILIZATION FEATURE

PRIORITY

This application is a continuation of U.S. patent application Ser. No. 17/871,491, filed Jul. 22, 2022, now U.S. Pat. No. 12,048,586, which claims the benefit of priority to U.S. Provisional Application No. 63/225,278, filed Jul. 23, 2021, and to U.S. Provisional Application No. 63/235,000, filed Aug. 19, 2021, each of which is incorporated by reference in its entirety into this application.

SUMMARY

Briefly summarized, embodiments disclosed herein are directed to a triphalangeal ultrasound probe stabilization feature. Current ultrasound systems include a probe supported between one or more triphalangeal digits (e.g. fingers) and a biphalangeal digit (e.g. thumb). Often a user is required to tension or stabilize the skin of the patient using the same hand that is holding the probe to provide a clear image. Further the probe often includes one or more controls, buttons, dials, etc., disposed thereon to operate various features of the ultrasound system. The user is required to both manipulate the probe, tension the skin and/or operate the controls with a single hand, all while preventing the probe from moving accidentally, which may affect the image quality.

Embodiments disclosed herein are directed to a stabilization feature configured to allow the user to grasp and manipulate the ultrasound probe with one or more fingers and without requiring any opposing pressure applied to the probe by the thumb. As such, the thumb of the user is free to either tension/stabilize the skin, or operate any controls using the thumb, independently of any manipulation of the probe by the fingers.

Disclosed herein is a stabilization system for a medical device including, a stabilization feature configured to engage the medical device and facilitate grasping and manipulating the medical device using one or more fingers, the stabilization feature having, a first portion configured to be grasped by the one or more fingers of a user, and a second portion configured to be coupled to the medical device.

In some embodiments, the second portion is integrally formed with the body of the medical device. In some embodiments, the second portion is releasably coupled with the body of the medical device. In some embodiments, the second portion is coupled to the body of the medical device with one of a threaded engagement, a clip and detent, adhesive, magnetic, interference fit, press-fit, or snap-fit engagement. In some embodiments, the first portion includes one of a post, a finger hook, a finger strap, an articulated finger strap, or a finger loop.

In some embodiments, the post includes a post head defining a larger diameter than the post, the post is configured to be grasped between a first finger and a second finger. In some embodiments, the finger hook includes a loop portion configured to engage a first finger, and a lip portion configured to engage a second finger. In some embodiments, the finger strap extends substantially parallel to a longitudinal axis of the body of the medical device and includes a rigid, flexible or elastically deformable material. In some embodiments, the finger strap is coupled to the body at a first end by a first probe strap and at a second end by a second probe strap, one or both of the first probe strap and the second probe strap including a plastic, polymer, elastomer, woven material, elasticated woven material, non-woven material, buckle, snap fastener, hook and loop, or a zip tie.

In some embodiments, the articulated finger strap includes a first end hingedly coupled to the body of the medical device, and a second end slidably engaged with the body, the articulated finger strap transitionable between an extended position and a retracted position. In some embodiments, the finger loop is formed of an elastically deformable material. In some embodiments, the finger loop is formed of a rigid material and is coupled to the body of the medical device with one of a hinge or a swivel. In some embodiments, the first portion is slidably engaged with the second portion along an axis extending parallel to a surface of the body of the medical device. In some embodiments, the stabilization system further includes a locking mechanism configured to selectively lock the first portion relative to the second portion.

In some embodiments, the second portion encircles a longitudinal axis of the medical device and engages a distal portion of the medical device in an interference fit. In some embodiments, the stabilization system further includes an aperture disposed in a distal end of the second portion and configured to align with a lens of the distal portion. In some embodiments, the stabilization system further includes a gel pad disposed within the aperture. In some embodiments, the second portion includes a needle guide configured to slidably engage a needle and align an axis thereof at a predetermined angle.

In some embodiments, the medical device is an ultrasound probe. In some embodiments, the second portion is configured to be coupled to both a body of the medical device and a sheath extending therebetween, the sheath configured to provide a sterile barrier between the medical device and the second portion. In some embodiments, the first portion is configured to be grasped by one or more fingers of a user through a sheath, wherein the sheath extends between the first portion and the one or more fingers of the user to provide a sterile barrier therebetween. In some embodiments, the stabilization system further includes a sheath integrally formed with the second portion and extending from an edge thereof, the sheath and the second portion co-operating to form a sterile barrier between the probe and the one or more fingers. In some embodiments, the stabilization system further includes a second stabilization feature coupled to the medical device.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figures 1A, 1B:
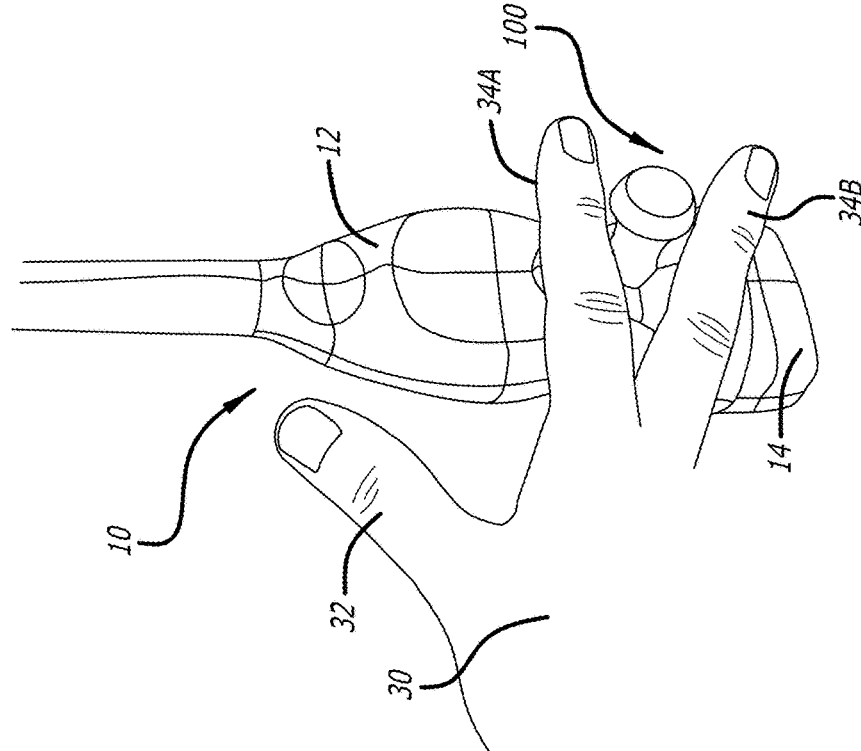
FIG. 1A shows a perspective view of an ultrasound probe including a stabilization feature, in accordance with embodiments disclosed herein.
FIG. 1B shows a perspective view of an ultrasound probe including a stabilization feature being held by a user, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a needle 40 (FIG. 5A) disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal end portion, or the proximal length of the needle can include the proximal end of the needle; however, the proximal portion, the proximal end portion, or the proximal length of the needle need not include the proximal end of the needle. That is, unless context suggests otherwise, the proximal portion, the proximal end portion, or the proximal length of the needle is not a terminal portion or terminal length of the needle.

With respect to "distal," a "distal portion" or a "distal end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal end portion, or the distal length of the needle can include the distal end of the needle; however, the distal portion, the distal end portion, or the distal length of the needle need not include the distal end of the needle. That is, unless context suggests otherwise, the distal portion, the distal end portion, or the distal length of the needle is not a terminal portion or terminal length of the needle.

To assist in the description of embodiments described herein, as shown in FIG. 1A, a longitudinal axis extends substantially parallel to an axial length of the probe 10. A lateral axis extends normal to the longitudinal axis, and a transverse axis extends normal to both the longitudinal and lateral axes. As used herein, a horizontal plane extends along the lateral and transverse axes, substantially parallel to a skin surface 20. A vertical plane extends normal to the horizontal plane.

Unless defined otherwise, all technical and scientific terms used herein have the same meaning as commonly understood by those of ordinary skill in the art.

Embodiments described herein are directed to a stabilization feature 100 configured to be coupled to an ultrasound probe ("probe") 10, or similar medical device, and to allow a user to grasp and manipulate the probe 10 using only one or more triphalangeal digits (i.e. "fingers") 34. As such, a user does not need to apply any pressure to the probe using a biphalangeal digit (i.e. "thumb") 32 leaving the thumb 32 free for other tasks, e.g. tensioning/stabilizing the skin proximate the probe 10, or operating one or more controls disposed on the probe 10.

FIGS. 1A-1B show an exemplary environment of use for a stabilization feature 100. As will be appreciated, embodiments of the stabilization device 100 can be used with various ultrasound probes 10, or similar medical devices, the probe 10 is an exemplary medical device and not intended to be limiting. Exemplary medical devices can include, but not limited to tracking devices, needle guides, surgical tools, endoscopes, catheter placement devices, or similar hand-held medical devices.

The probe 10 can generally include a body 12 extending axially along a longitudinal axis and including a probe head 14 disposed at a distal end thereof. The probe body 14 can be grasped by the user to manipulate the probe head 14 against a skin surface 20. The body 14 can extend substantially perpendicular to the skin surface 20. However, in an embodiment, the probe body 12 can be held at various angles relative to the skin surface 20. The probe head 14 can be configured to emit/detect signals, for example, emit ultrasonic acoustic signals and detect reflected acoustic signals. These signals and information can be transmitted to a console (not show) to determine an image.

In an embodiment, the probe 10 can include a stabilization feature 100 coupled to the probe 10, e.g. a probe body 12, and extending therefrom. As shown in FIG. 1B, the stabilization feature 100 can configured to be grasped by one or more fingers 34 to manipulate the probe 10 without requiring any pressure to be applied to the probe 10 by the thumb 32.

Figure 2A:
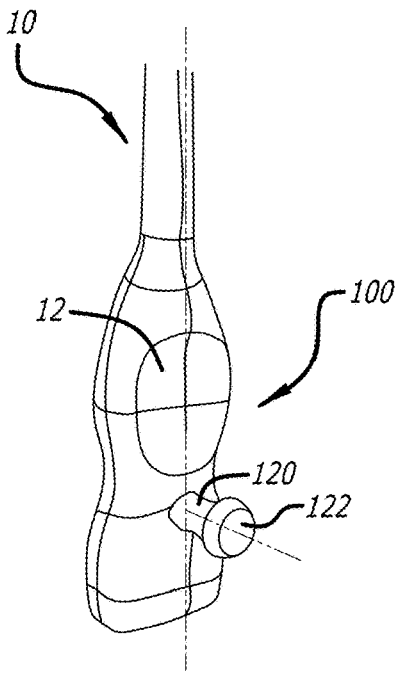
FIG. 2A shows a stabilization feature integrally formed with a medical device, in accordance with embodiments disclosed herein.

FIGS. 2A-2J show various configurations of the stabilization feature 100. In an embodiment, as shown in FIG. 2A, a stabilization feature 100 can be formed integrally with the probe 10 to create a single monolithic piece. In an embodiment, the stabilization feature 100 can extend from a side surface of the probe body 12 and can extend substantially perpendicular to a longitudinal axis. However, it will be appreciated that the stabilization feature 100 can extend from one or more surfaces and can extend at various angles relative to the longitudinal axis and still fall within the scope of the present invention.

As shown in FIG. 2A, the probe 10 can include a single stabilization feature 100. However, it will be appreciated that embodiments disclosed herein can include one or more stabilization features 100 each configured to engage one or more fingers 34. In an embodiment, each of the one or more stabilization features 100 can be identical. In an embodiment, each of the one or more stabilization features 100 can be different, different sizes, and/or include various different features and embodiments, as disclosed herein.

In an embodiment, the stabilization feature 100 can include one or more posts, loops, hooks, flexible tethers, or the like, as described in more detail herein. In an embodiment, the stabilization feature 100 can be a rigid or static structure, as described in more detail herein. In an embodiment, the stabilization feature 100 can be a flexible, articulated, or adjustable structure, as described in more detail herein.

In an embodiment, the stabilization feature 100 can be formed of the same material as the probe 10. In an embodiment, the stabilization feature 100 can include one or more different materials from that of the probe 10, and can each provide different mechanical properties. In an embodiment, the stabilization feature 100 can include one or more of a plastic, polymer, elastomer, metal, alloy, composite, combinations thereof, or the like.

In an embodiment, the stabilization feature 100 can include one or more of different texturing, ribbing, contouring, one or more materials including different frictional coefficients, durometers, elastic tension properties, or one or more adjustable portions configured to facilitate grasping of the stabilization feature 100 by one or more fingers 34.

In an embodiment, as shown in FIG. 2A, the stabilization feature 100 can include a post 120 extending from the probe body 12 and extending substantially perpendicular to a longitudinal axis of the probe body 12. In an embodiment, the axis of the post 120 can extend at an angle relative to the longitudinal axis of the probe body 12. The post 120 can include a cylinder having a substantially circular cross sectional shape. However, it will be appreciated that other cross-sectional shapes, including elliptical, square, triangular, hexagonal, or any regular or irregular closed-curve polygonal shapes are also contemplated to fall within the scope of the present invention. In an embodiment, the post 120 can define a first diameter. In an embodiment, the post can further include a post head 122 disposed at an opposite end of the post from the probe body 12. In an embodiment, the post head 122 can define a substantially spherical or ellipsoidal shape. However, it will be appreciated that the post head 122 can include various regular or irregular, curved or faceted, three-dimensional shapes. In an embodiment, an outer diameter of the post head 122 can be larger than an outer diameter of the post 120.

In an exemplary method of use, as shown in FIG. 1B, the post 120 can be grasped between a first finger 34A and a second finger 34B. The user can then manipulate an axis of the probe body 12 using only these two fingers 34A, 34B without requiring any opposing pressure from the thumb 32.

In an embodiment, the post 120 can articulated to be extendable from a surface of the probe body 12. For example, the post 120 can be slidably engaged with the probe 10 along an axis extending at an angle relative to the longitudinal axis. In use, a user can grasp the post head 122, or a gripping feature (e.g. tab, loop, flange, etc.) extending therefrom, and can pull the post out of the probe body 12, transitioning the post 120 from a retracted position to an extended position. A clip or similar mechanism can be configured to retain the post 120 in one of the extended or retracted positions. In an embodiment, the post 120 can be collapsible on itself, (i.e. a first portion of the post 120 can be slidably engaged and received within a second portion of the post 120), and can be transitional between an extended and a retracted position. In an embodiment, the post 120 can include a pleated or telescopic portion configured to transition the post 120 between the extended and the retracted position. In the retracted position, the post 120 can lie substantially flat against a surface of the probe 10. In embodiment, the articulated post 120 can include a biasing member configured to bias the post 120 towards one or both of the extended and the retracted positions. In an embodiment, the articulated post 120 can be bistable in both the extended and the retracted positions.

Advantageously, the post 120 configured to transition between an extended or collapsed configuration can allow the user to fold the stabilization feature substantially flush with a surface of the probe 10 when not in use to prevent the stabilization feature 100 from obstructing usage of the probe 10. The user can then selectively extend the stabilization feature 100 from the surface of the probe 10 to the extended position, as required.

Figure 2B:
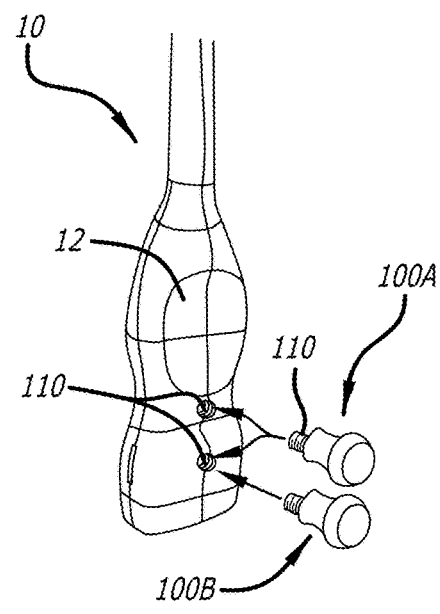
FIG. 2B shows a stabilization feature threadably attached with a medical device, in accordance with embodiments disclosed herein.

In an embodiment, as shown in FIG. 2B, the stabilization feature 100 can include a threaded engagement structure 110 configured to threadably engage the stabilization feature 100 with the probe 10. As shown, the stabilization feature can include a male threaded engagement and the probe body 12 can include one or more female threaded engagements. However, as will be appreciated, the stabilization feature 100 can include a female threaded engagement configured to engage one or more male threaded engagements disposed on the probe body 12.

Advantageously, one or more stabilization features 100 can be selectively coupled to the probe 10 at one or more positions along a surface of the probe body 12. Similarly, the stabilization feature 100 can be selectively removed from the probe 10 as preferred by the user. For example, a first stabilization feature 100A including a post 120 and post head 122 can be coupled at a first position, a second stabilization feature 100B can be coupled to a second position. The user can then grasp the one or more stabilization features 100A, 100B with one or more fingers 34, as described herein. As will be appreciated, the threaded engagement structure 110 can include any combination of threaded engagement, bayonet fit, interference fit, or press-fit engagement, or the like.

Figure 2C:
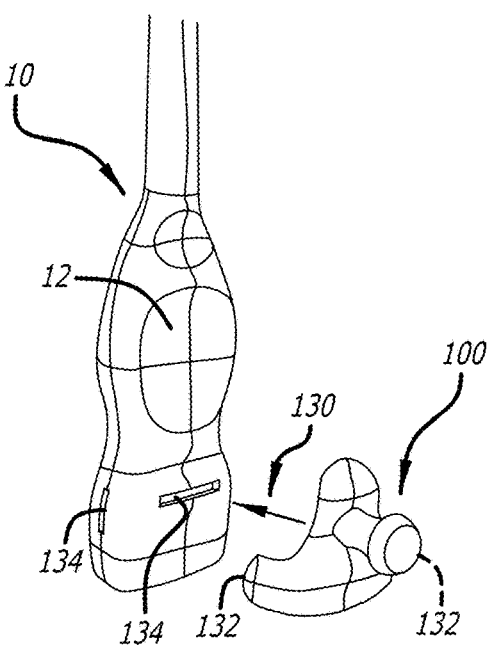
FIGS. 2C-2D shows a stabilization feature selectively engaged with a medical device and including a clip and detent structure, in accordance with embodiments disclosed herein.
Figure 2D:
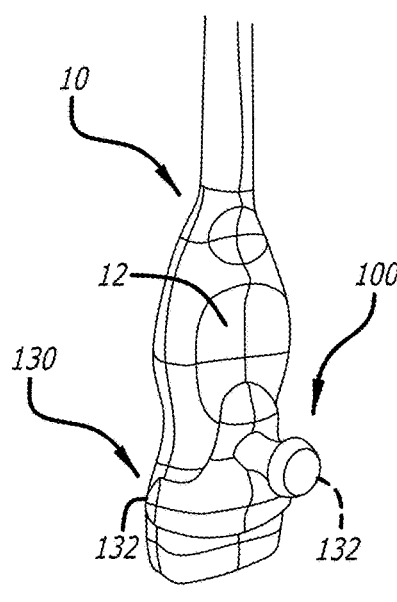

In an embodiment, as shown in FIGS. 2C-2D the stabilization feature 100 can include a clip and detent engagement structure 130 configured to selectively engage the stabilization feature 100 with the probe 10. In an embodiment, one of the stabilization feature 100 or the probe body 12 can include a clip 132 configured to engage a detent 134 disposed on one of the probe body 12 or the stabilization feature 100, or combinations thereof. For example, as shown, the stabilization feature 100 can include one or more clips 132 each configured to engage a detent 134 disposed on the probe body 12 to releasably secure the stabilization feature 100 thereto. It will be appreciated, however, that the probe body 12 can include one or more clips 132 each configured to engage one or more detents 134 disposed on the stabilization feature 100, or combinations thereof. As will be appreciated, the clip and detent engagement structure 130 can include any combination of clips, barbs, latches, detents, hooks, lock-and-key engagements, keyed lock connection plates, interference fit, snap-fit engagements, bayonet fit engagements, combinations thereof, or the like.

Advantageously, the clip and detent engagement feature 130 can allow the user to selectively engage the stabilization feature 100 with the probe 10 as required, as described herein. As will be appreciated, similar clip and latch engagement structures configured to selectively secure the stabilization feature 100 to the probe 10 are also contemplated. Advantageously, the clips 132 can be designed to engage pre-existing detents, protrusions, edges, lips, flanges, or similar structures already disposed on the probe 10 without requiring any pre-existing or specially designed features to be disposed on the probe 10. Advantageously, having the stabilization feature 100 including a clip 132 configured to engage a portion of the probe 10, e.g. a detent 134 disposed thereon, allows for easier cleaning of the probe 10.

Figure 2E:
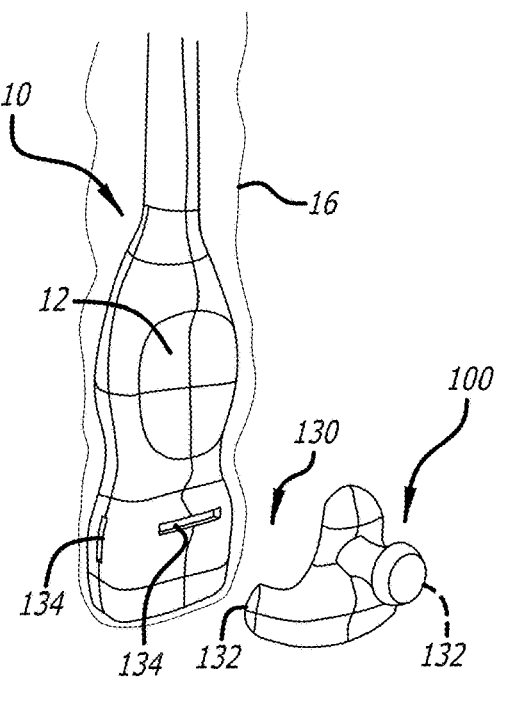
FIGS. 2E-2F shows a stabilization feature selectively engaging a medical device through a sheath, in accordance with embodiments disclosed herein.
Figure 2F:
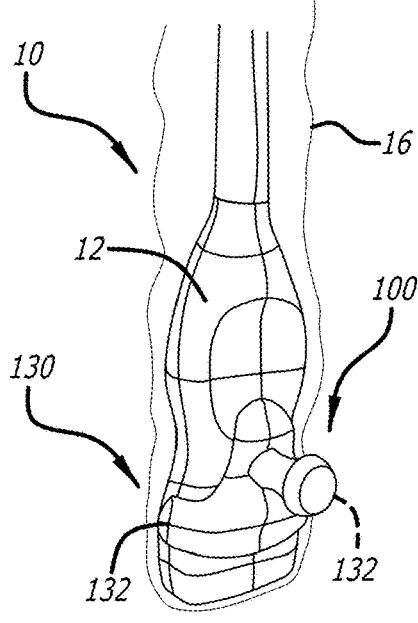

In an embodiment, as shown in FIGS. 2E-2F, the stabilization feature 100 can be configured to engage the probe 10 while the probe 10 is disposed within a sheath 16. As used herein a sheath 16 can include any flexible, thin-film barrier configured to maintain a sterile barrier between the probe 10 and the surrounding environment. In an embodiment, the stabilization feature 100 can selectively engage the probe 10 through the barrier 16. Worded differently the barrier 16 can extend between the probe body 12 and the stabilization feature 100 and maintain a sterile barrier therebetween while the stabilization feature 100 engages the probe body 12 to allow the user to manipulate the probe 10 as described herein. In an embodiment, the stabilization feature 100 can include a clip and detent 130 engagement to couple the stabilization feature 100 to the probe 10, as described herein. However, it will be appreciated that other engagement structures capable of coupling the stabilization feature 100 to the probe 10 while maintaining a sterile barrier therebetween are also contemplated. In an embodiment, a portion of the stabilization feature 100, e.g. a clip 132, can pierce the sheath 16 to engage the probe 10 directly and can co-operate with the sheath 16 to maintain a sterile barrier between the probe 10 and the surrounding environment.

Figure 2G:
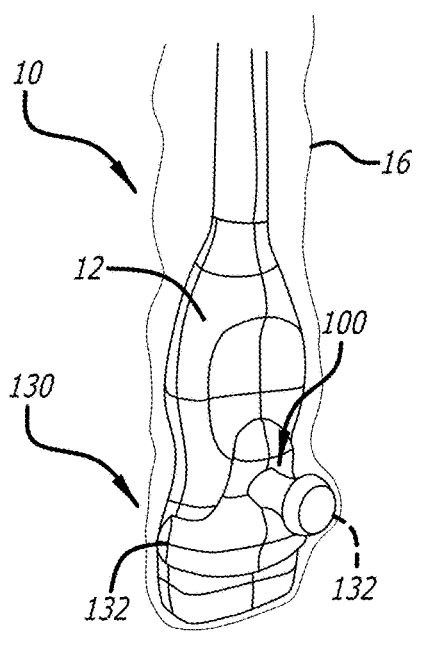
FIG. 2G shows a stabilization feature selectively engaged with a medical device within a sheath, in accordance with embodiments disclosed herein.

In an embodiment, as shown in FIG. 2G, the stabilization feature 100 can be selectively coupled with the probe 10, or formed integrally therewith, as described herein. The probe 10 and the stabilization feature 100 assembly can then be disposed within the sterile barrier 16. Advantageously, the stabilization feature 100 can be configured to be grasped by the user through the flexible sheath 16. As such, the sheath 16 can maintain a sterile barrier between the stabilization feature 100 and the user's hand 30.

In an embodiment, the stabilization feature 100 can be formed integrally with the sheath 16 and can co-operate to define a sterile barrier. For example, the stabilization feature 100 can selectively engage the probe body 12, as described herein. A flexible, thin-film sheath 16 can extend from an edge of the stabilization feature 100 and can encircle the probe 10 to provide a sterile barrier between the probe 10 and the surrounding environment as described herein. As such, the sheath 16 does not extend between the stabilization feature 100 and the probe 10 and so does not interfere with securing the stabilization feature 100 thereto. Further the sheath 16 does not extend between the stabilization feature 100 and the users hand 30 and so does not affect the user's grasp of the stabilization feature 100. Further still a sterile barrier is still maintained between probe 10 and the surrounding environment.

Figure 2H:
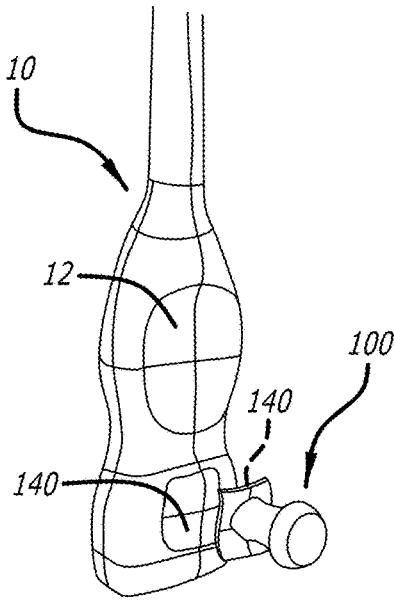
FIG. 2H shows a stabilization feature adhesively engaged with a medical device, in accordance with embodiments disclosed herein.

In an embodiment, as shown in FIG. 2H, one or both of the probe 10 and the stabilization feature 100 can include an adhesive surface 140. The adhesive surface 140 can be configured to adhere the stabilization feature 100 to the probe body 12. Advantageously, the adhesive surface 140 can selectively couple the stabilization feature 100 to the probe 10 without requiring any pre-existing, or specially designed engagement structure disposed on the probe 10. As such, the stabilization feature 100 can be coupled to any pre-existing probe 10. In an embodiment, the stabilization feature 100 can be adhered to a sheath 16 or similar sterile barrier 16 that in turn is fixedly attached, coupled or adhered to the probe body 12. In an embodiment, the adhesive surface 140 can include various strengths of pressure reactive adhesives, bonding, or the like. In an embodiment, the stabilization feature 100 can be adhered to a portion of a second stabilization feature that is in turn attached, coupled or adhered to the probe body 12.

Figure 2J:
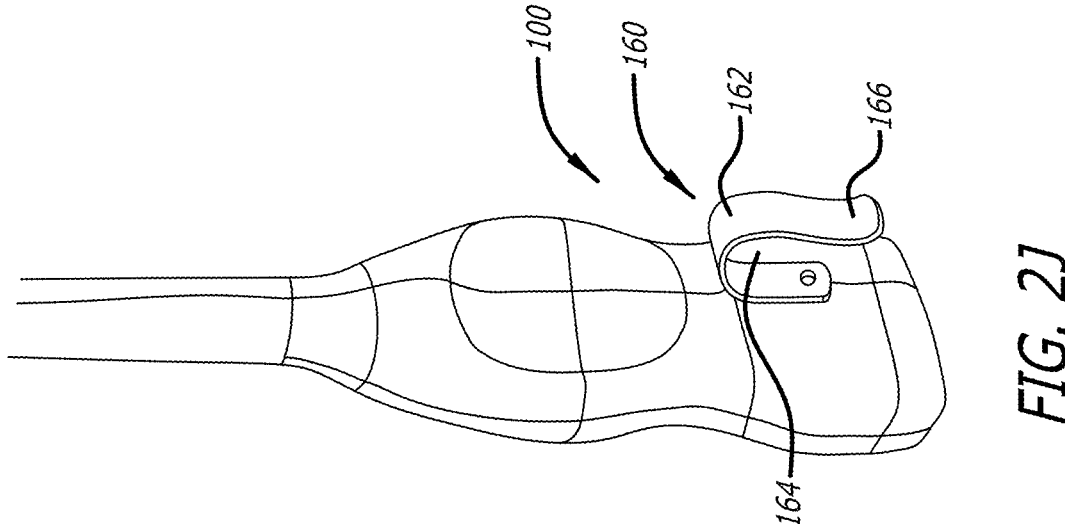
FIG. 2J shows a finger hook stabilization feature engaged with a medical device, in accordance with embodiments disclosed herein.
Figure 2I:
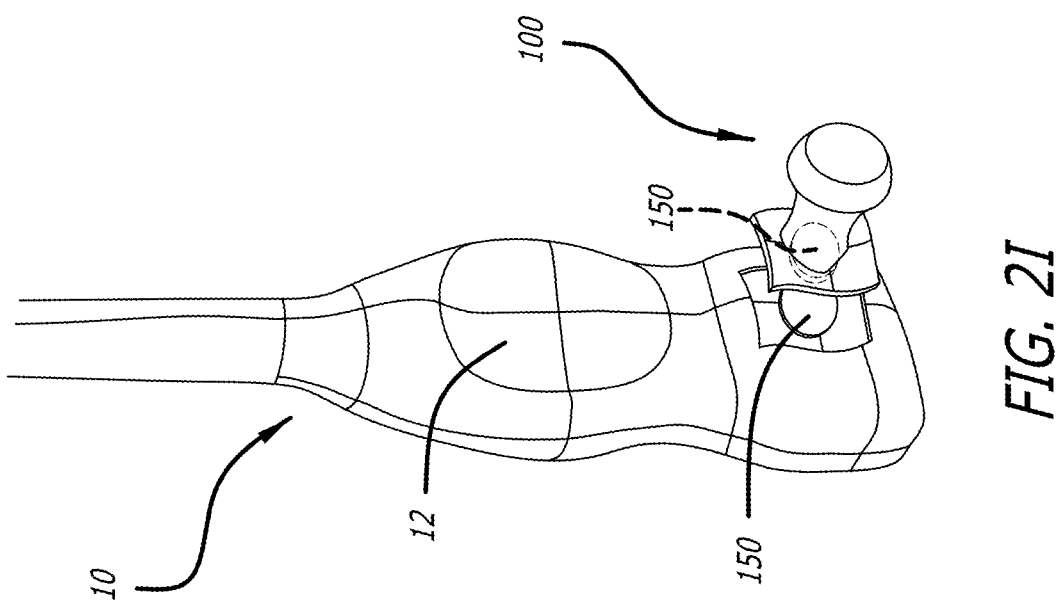
FIG. 2I shows a stabilization feature magnetically engaged with a medical device, in accordance with embodiments disclosed herein.

In an embodiment, as shown in FIG. 2I, one or both of the probe 10 and the stabilization feature 100 can include a magnet 150. The magnet 150 can be configured to selectively couple the stabilization feature 100 to the probe body 12. In an embodiment, the stabilization feature 100 can include a magnet 150 configured to engage a metallic, or ferrous material coupled with the probe 10. Similarly, in an embodiment, the probe 10 can include a magnet 150 configured to engage a metallic, or ferrous material coupled with the stabilization feature 100. In an embodiment, the magnet 150 can be a permanent magnet or an electromagnet.

Advantageously, the magnet 150 can selectively couple the stabilization feature 100 to the probe 10 without requiring any pre-existing, or specially designed engagement structure disposed on the probe 10. As such, the stabilization feature 100 can be coupled to any metallic or ferrous portion of pre-existing probes 10. Alternatively a metallic portion or second magnet 150 can be coupled to the probe and can be configured to engage a first magnet 150 disposed on the stabilization feature 100. Advantageously, the stabilization feature 100 including the magnet 150 can be coupled to a probe 10 that is disposed within a sheath 16 or similar sterile barrier. The sheath 16 can extend between the probe 10 and the stabilization feature 100, maintaining a sterile barrier therebetween, while the magnet 150 couples the stabilization feature 100 to the probe 10, as described herein.

As shown in FIGS. 2B-2I, the stabilization feature 100 includes a post 120 configured to be grasped by a user by one or more fingers 34, as described herein. However, it will be appreciated that embodiments of stabilization feature 100 described herein can include one or more flexible or rigid, static or adjustable, posts, finger loops, finger hooks, flexible tethers, combinations thereof, or the like, as described herein.

In an embodiment, as shown in FIG. 2J, the stabilization feature can include a finger hook 160. The finger hook 160 can extend from a surface of the probe body 12 and can include a loop portion 162 that extends through an arc distance of between 100° and 350°. The loop portion 162 can define a finger channel 164 configured to receive a first finger 34A therethrough and allow a user to grasp the stabilization feature 100 with a single finger 34. An inner surface of the loop portion 162 can define a radius of curvature that substantially matches a radius of curvature of an outer surface of a finger 34. In an embodiment, the radius of curvature of the loop portion 162 can be less than a radius of curvature of an outer surface of a finger 34. In an embodiment, the finger hook 160 can be formed of a resilient material. As such, a portion of the finger hook 160 can deflect slightly as the finger 34 engages the finger hook 160 and can grip the user's finger 34.

In an embodiment, the finger hook 160 can further include a lip portion 166. In an embodiment, a second finger 34B can engage the lip portion 166 allowing a user to grasp the stabilization feature 100 and manipulate the probe 10 using two or more fingers 34. In an embodiment, the finger hook 160 can be foldable between an extended position (FIG. 2J) and a retracted position where the finger hook 160 can lie substantially flat against the probe body 12.

Figure 3A:
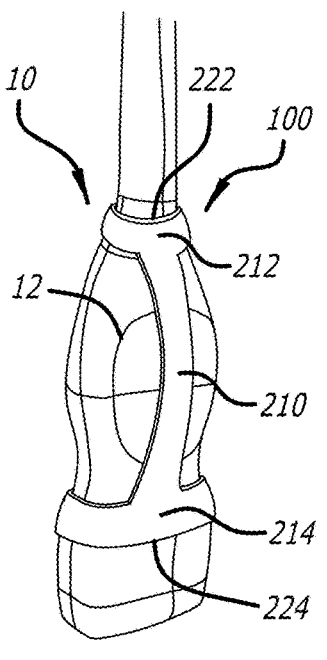
FIGS. 3A-3B show a finger strap engagement feature coupled with a medical device, in accordance with embodiments disclosed herein.
Figure 3B:
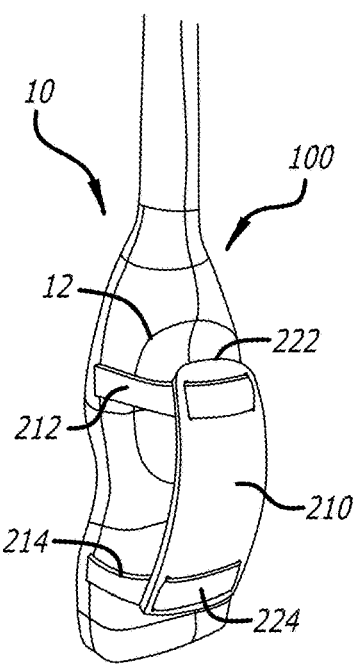
Figure 3C:
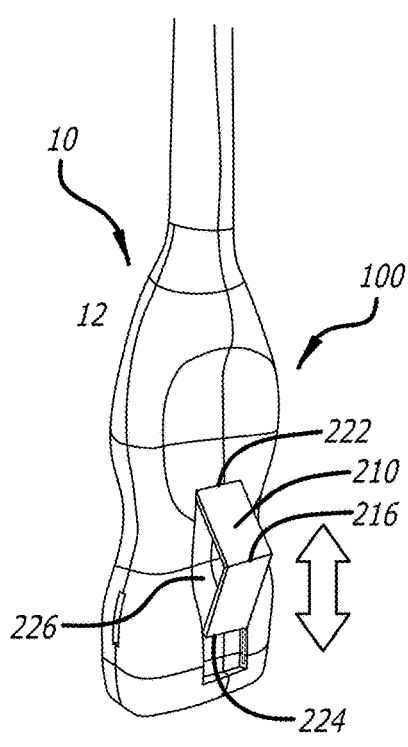
FIG. 3C shows an articulated finger strap engagement feature coupled with a medical device, in accordance with embodiments disclosed herein.

In an embodiment, as shown in FIGS. 3A-3C, the stabilization feature 100 can include a finger strap 210. The finger strap 210 can extend substantially parallel to a longitudinal axis of the probe body 12. In an embodiment, the finger strap 210 can extend at an angle relative to the longitudinal axis of the probe body 12. The finger strap 210 can be coupled to the probe 10 at one or both of a first end 222 and a second end 224. In an embodiment, the finger strap 210 can be formed of a flexible material. In an embodiment, the finger strap 210 can be formed of an elastically deformable material. In an embodiment, the finger strap 210 can be formed of a plastic, polymer, elastomer, woven material, elasticated woven material, non-woven material, synthetic material, organic material, leather, faux leather, rubber, silicone rubber, combinations thereof, or the like.

In an embodiment, the first end 222 can be coupled to the probe 10 using a first probe strap 212 and the second end 224 can be coupled to the probe 10 using a second probe strap 214. Each probe strap 212, 214 can encircle a portion of the probe body 12 about the longitudinal axis. In an embodiment, each probe strap 212, 214 can be formed of the same material as the finger strap 210. In an embodiment, each probe strap 212, 214 can be formed of plastic, polymer, elastomer, woven material, elasticated woven material, non-woven material, synthetic material, organic material, leather, faux leather, rubber, silicone rubber, combinations thereof, or the like. In an embodiment, the probe strap 212, 214 can be secured about the probe body with an interference fit, buckle, snap fastener, hook and loop (e.g. Velcro™), zip tie, combinations thereof, or the like. Advantageously, the probe straps 212, 214 can couple the finger strap 210 to the probe 10 without requiring any pre-designed structures disposed on the probe 10, allowing the finger strap 210 to be coupled to any pre-existing probe 10. In an embodiment, as shown in FIG. 3B, the finger strap 210 can be formed of a flexible material, a resilient material, or of a substantially rigid material. In an embodiment, the finger strap 210 can be formed of a plastic, polymer, leather, metal, alloy, composite, combinations thereof, or the like. Further, one or both of the first probe strap 212 and the second probe strap 214 can be formed of an elastically deformable material.

In an exemplary method of use, a user can elastically deform one or more of the finger strap 210, the first probe strap, or the second probe strap 214 to allow one or more fingers 34 to pass between the finger strap 210 and the probe body 12. Advantageously, the finger strap 210 can be coupled with any pre-existing probe body 12 and allow a user to grasp and manipulate the probe 10 using one or more fingers 34. Further, the finger strap 210 can be held flush against the surface of the probe body 12 when not in use.

In an embodiment, the finger strap 210 can be coupled to the probe body 12 using fasteners, screws, bolts, adhesive, bonding, welding, magnets, clips and detent, interference fit engagement, press-fit engagement, snap-fit engagement, combinations thereof, or the like.

In an embodiment, as shown in FIG. 3C, the stabilization feature 100 can include an articulated finger strap 210. In an embodiment, the finger strap 210 can be formed of a flexible material. In an embodiment, the finger strap 210 can be formed of a rigid material and can include one or more hinges 216 configured to allow the rigid finger strap 210 to articulate. The hinge 216 can be a mechanical hinge or a living hinge. In an embodiment, a first end 222 of the finger strap 210 can be hingedly coupled to the probe body 12. A second end 224 of the finger strap 210 can be slidably engaged with the probe body 12. In an embodiment, the articulated finger strap 210 can transition between a retracted position and an extended position. In the retracted position, the finger strap 210 can lie flat against a surface of the probe body 12. In an embodiment, in the retracted position, the finger strap 210 can be disposed within a recess 226 disposed within surface of the probe body 12 such that a surface of the finger strap 210 lies flush with the probe body 12.

As the articulated finger strap 210 transitions from the retracted position to the extended position, one or both of the first end 222 and the hinge 216 can rotate. Further, the second end 214 can slide relative to the probe body 12. As such, the finger strap 210 can articulate from a substantially flat configuration to an angled configuration as shown in FIG. 3C. In the extended configuration, a user can slide a finger 34 between the finger strap 210 and the probe body 12 to grasp and manipulate the probe as described herein. Advantageously, the user can selectively transition the finger strap 210 to the retracted position when not in use to avoid obstructing the use of the probe 10. As such the stabilization feature 100 can be configured to actuate to protrude from a condensed form factor.

Figure 4B:
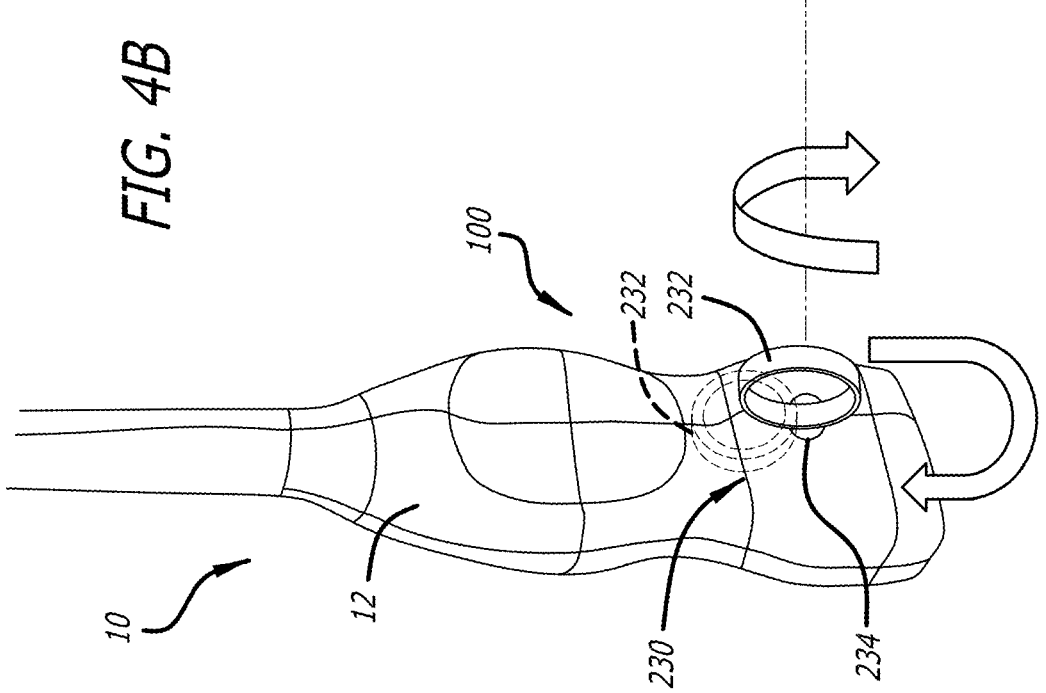
FIG. 4B shows an adjustable loop stabilization feature coupled to a medical device, in accordance with embodiments disclosed herein.
Figure 4A:
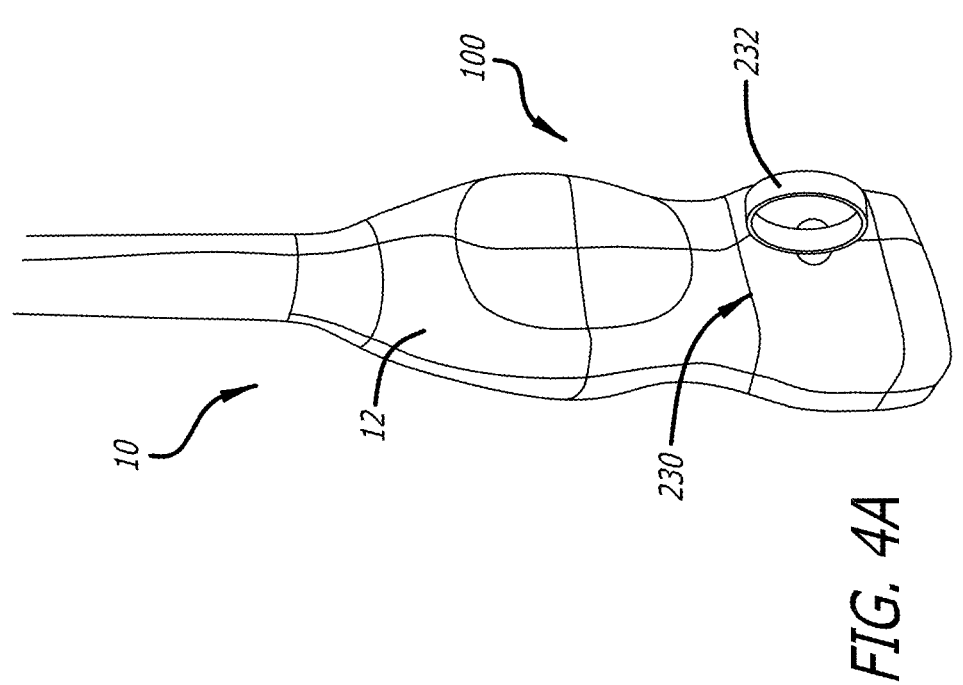
FIG. 4A shows a flexible loop stabilization feature coupled to a medical device, in accordance with embodiments disclosed herein.

In an embodiment, as shown in FIGS. 4A-4B, the stabilization feature 100 can include a finger loop 230. In an embodiment, the finger loop 230 can include a ring 232 extending annularly and extending over a plane angled relative to the surface of the probe body 12. The ring 232 can be configured to receive one or more fingers 34 therethrough. In an embodiment, the finger loop 230 can include one or more rings 232, each of which can be configured to receive one or more fingers 34 therethrough. In an embodiment, the finger loop 230 can be fixedly coupled relative to the probe body 12. In an embodiment, the finger loop 230 can be integrally molded with the probe body 12. In an embodiment, the finger loop 230 can be formed from a different material from that of the probe body 12 and coupled thereto, as described herein. In an embodiment, the finger loop 230 can be formed of a flexible, compliant or elastically deformable material including plastic, polymer, elastomer, rubber, silicone rubber, or the like. Advantageously, the flexible properties of the finger loop 230 can allow the finger loop 230 to twist and conform to different positions of the finger 34 relative to the probe body 12, as the user grasps and manipulates the probe 10.

In an embodiment, a first diameter of the elastically deformable ring 232, in an unstressed state, can be equal to or larger than a diameter of a finger 34. Advantageously, a user can easily slide one or more fingers through the ring 232. In an embodiment, a first diameter of the elastically deformable ring 232, in an unstressed state, can be equal to or slightly smaller than a diameter of a finger 34. The ring 232 can be elastically deformable to a second diameter larger than the first diameter. As such, a user can stretch the ring 232 over the finger 34 and the ring 232 can engage the finger 34 in an interference fit. Advantageously, the ring 232 can secure the probe 10 to the finger 34 without the user having to actively grasp the stabilization feature 100. In an embodiment, the ring 232 can include one or more texturing, ribbing, contouring, or the like to facilitate grasping the stabilization feature 100.

In an embodiment, as shown in FIG. 4B, the finger loop 230 can include a swivel joint 234 configured to rotationally couple the ring 232 with the probe body 12. As such, the ring 232 can rotate and pivot about an axis extending at an angle to the longitudinal axis of the probe body 12 and can orient the ring 232 to one or more positions. Advantageously, the swivel joint 234 can allow the finger loop 230 to rotate and conform to different positions of the finger 34 as the user grasps and manipulates the probe 10. In an embodiment, the swivel 234 can be rotationally and hingedly coupled to the probe body 12. As such, the ring 232 can transition between an extended position (FIGS. 4A-4B) and a retracted position where the ring 232 lies flat against a surface of the probe body 12, as shown in dashed outline in FIG. 4B. In an embodiment, the hinged swivel 234 can include a ball and detent mechanism configured to allow the ring 232 to be pivoted about an axis of the swivel joint 234 between one or more predetermined positions. The ring 232 can also be folded between one or more predetermined positions between the extended position and the retracted position. As such, a user can pivot and fold the ring 232 between the one or more predetermined positions, and the ring 232 can remain in position until reposition by the user, to position and orient the ring 232 as preferred.

Figure 5B:
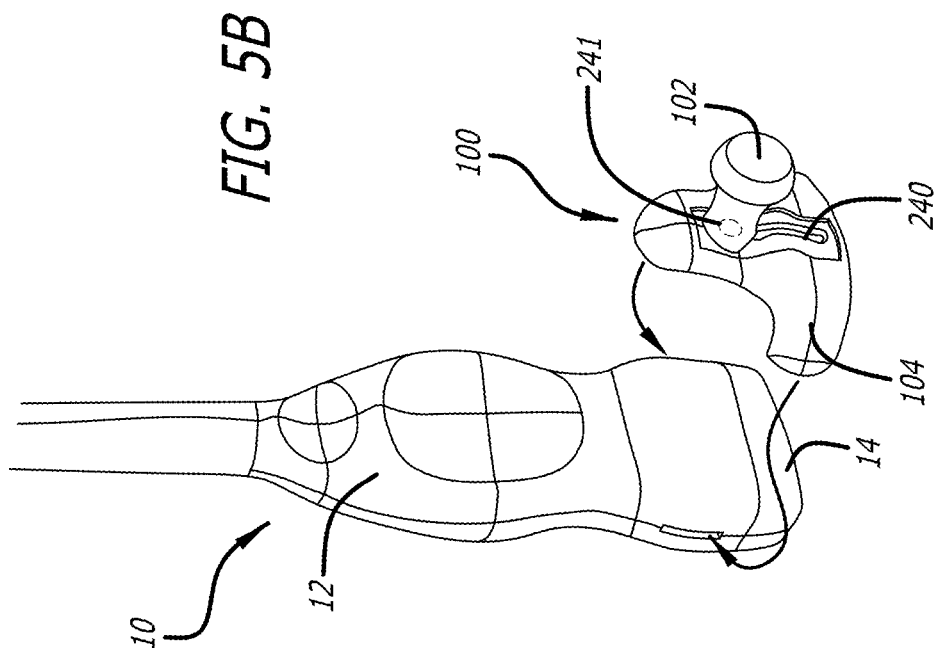
FIGS. 5A-5B show an adjustable stabilization feature coupled to a medical device and including a slidable portion, in accordance with embodiments disclosed herein.
Figure 5A:
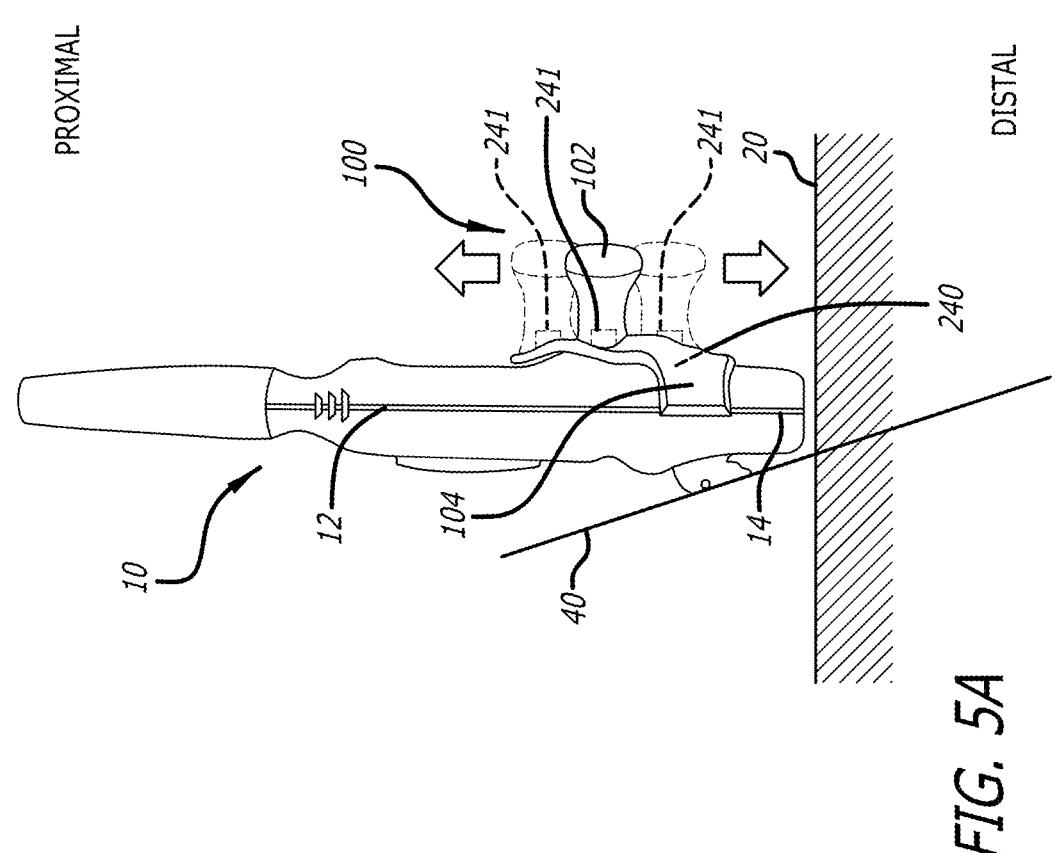

In an embodiment, as shown in FIGS. 5A-5B, the stabilization feature 100 can include a slide 240 configured to allow a first portion 102 of the stabilization feature 100 to slide relative to a second portion 104. In an embodiment, the first portion 102 can be configured to be grasped by one or more fingers 34 of a user, as described herein. In an embodiment, the second portion 104 can be configured to couple the stabilization feature 100 to the probe 10, as described herein.

In an embodiment, the slide 240 can be configured to allow the first portion 102 to slide relative to the second portion 104 along an axis extending substantially parallel to a surface of the probe body 12. As such, the slide 240 can allow the user to selectively modify the position of the first portion 102 relative to the second portion 104, e.g. a relative height, a side-to-side position, or at an angle there between. In an embodiment, the slide 240 can include a locking mechanism configured to allow a user to selectively lock the first portion 102 relative to the second portion 104. In an embodiment, the slide 240 can include a ball and detent mechanism 241 configured to allow a user to selectively slide and adjust the first portion 102 relative to the second portion 104 between one or more predetermined positions along an axis of the slide.

Figure 6B:
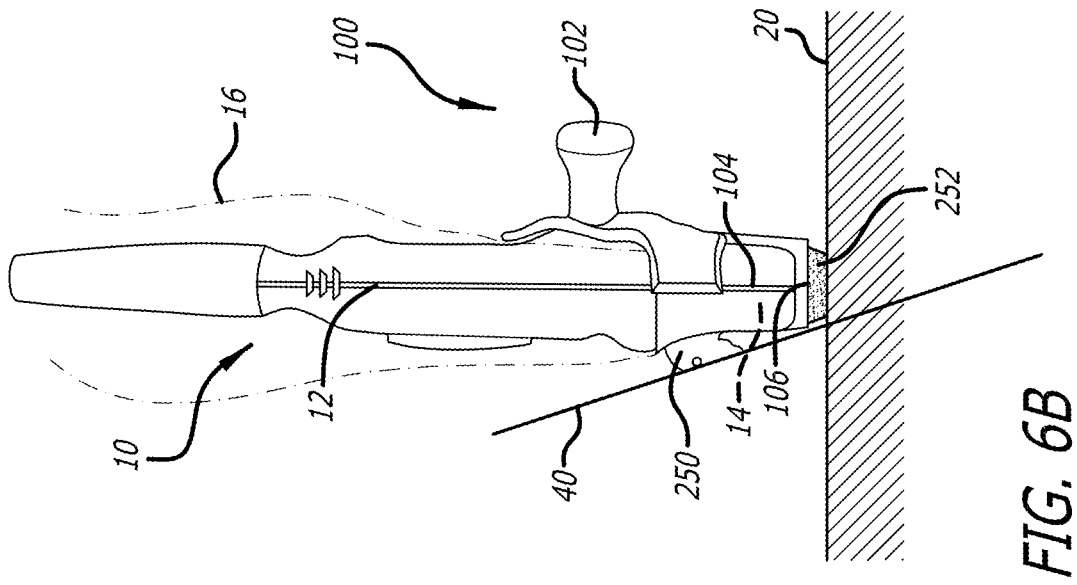
FIG. 6B shows a stabilization feature including a gel cap and an integrated sheath and coupled to a medical device, in accordance with embodiments disclosed herein.
Figure 6A:
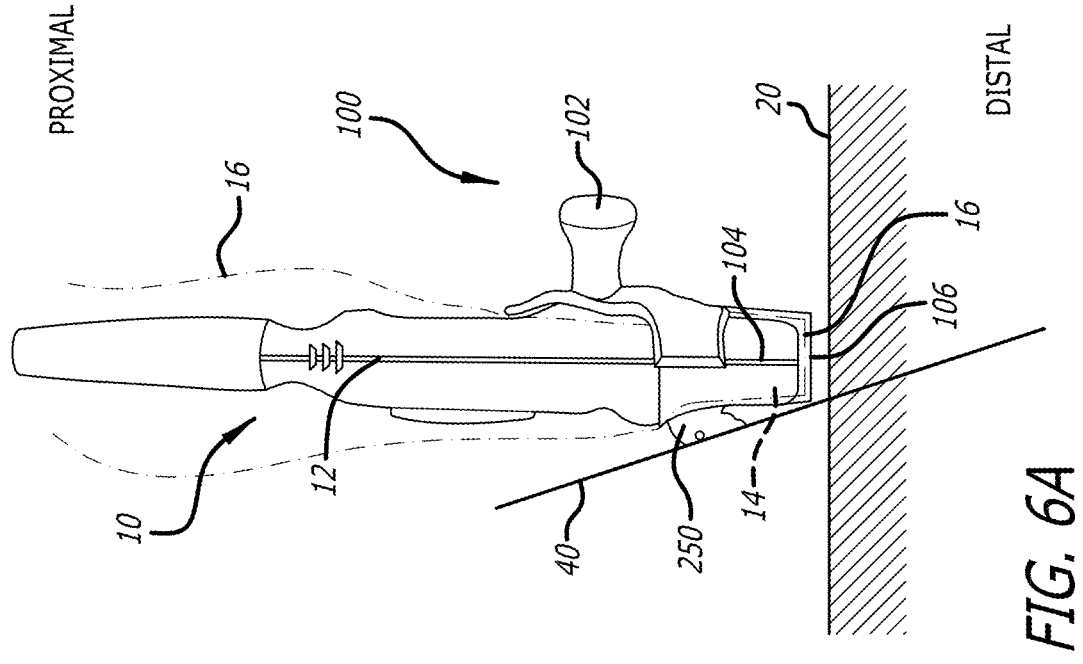
FIG. 6A shows a stabilization feature coupled to a medical device over a sheath and including a needle guide, in accordance with embodiments disclosed herein.

In an embodiment, as shown in FIGS. 6A-6B, the stabilization feature 100 can include a second portion 104 configured to engage a probe head 14 and couple the stabilization feature 100 to the probe 10 as described herein. In an embodiment, the second portion 104 can encircle the probe head 14 about a longitudinal axis. In an embodiment, the second portion 104 can be formed from a rigid or resilient material and can engage the probe head 14 in an interference fit, press-fit, snap-fit engagement, or the like. However, other engagements are also contemplated, as described herein.

In an embodiment, the second portion 104 of the stabilization feature 100 can engage the probe head 12 by sliding vertically upwards, on to the probe head 12. In an embodiment, the stabilization feature 100 can be disposed within a sterile packaging. The sterile packaging can maintain the stabilization feature 100 within a sterile environment during transport and storage. In an embodiment, the sterile packaging can include a frangible opening. In use, a clinician can grasp the stabilization feature 100 within the sterile packaging and can manipulate the stabilization feature 100 without compromising the sterility of the stabilization feature 100. The clinician can manipulate the probe 10 to urge a probe head 12 through the frangible opening to engage the second portion 104, as described herein. The clinician can then remove the probe head 12 and stabilization feature 100 assembly from the sterile packing, ready for use.

In an embodiment, the probe 10 including the probe head 12 can be disposed within a sheath 16 when urged through the frangible opening to maintain the probe 10 within an sterile environment. The stabilization feature 100 can then engage the probe 10 through or over the sheath 16 as described herein. In an embodiment, the probe 10 and the stabilization feature 100 can both be disposed within a sheath 16 when the probe head 12 is urged through the frangible opening. The stabilization feature 100 can be coupled to the probe 10 within the sheath 16.

In an embodiment, as shown in FIG. 6A, a distal end of the second portion 104 can define an aperture 106 configured to allow a portion of the probe head 14 to extend therethrough and engage a skin surface 20. In an embodiment, the stabilization feature 100 can further include a needle guide 250, configured to receive a needle 40, or similar elongate medical device. The needle guide 250 can slidably engage a needle 40 and align the needle 40 with one or more predetermined angles relative to an axis of the probe 10.

In an embodiment, a sheath 16 can extend between the probe body 12 and the second portion 104 of the stabilization feature 100 to provide a sterile barrier therebetween, as described herein. In an embodiment, a portion of the sheath 16 can extend across the aperture 106. In an embodiment, the second portion 104 can be configured to stretch the sheath 16 tightly across the aperture 106 or across the probe head 14 to conform the sheath 16 to the lens of the probe head 14. As such, any interference of signals, or the like, traversing the sheath 16 at the aperture 106 is minimized.

In an embodiment, as shown in FIG. 6B, the stabilization feature 100 can further include a gel cap 252 disposed within the aperture 106. The gel cap 252 can be formed of a compliant material and can be acoustically conductive. In use, the gel cap 252 can be compressed between the skin surface 20 and the probe head 14 and can facilitate transmission of the acoustic signals therebetween, through the aperture 106.

In an embodiment, as shown in FIG. 6B the sheath 16 can be formed integrally with the stabilization feature 100 and can extend from an edge thereof. In an embodiment, the sheath 16, second portion 104 of the stabilization feature 100, and gel cap 252, or combinations thereof, can co-operate to define a sterile barrier that encloses the probe 10.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A triphalangeal stabilization feature for an ultrasound probe having a longitudinal axis extending orthogonal to a skin engaging surface of the ultrasound probe, the triphalangeal stabilization feature comprising:
  a stationary member having a shape conforming to an outer surface of the ultrasound probe and a slot extending linearly along the longitudinal axis;
  a manipulation member slidingly coupled to the slot of the stationary member and extending away from the stationary member, the slot preventing sliding motion of the manipulation member at an angle to the longitudinal axis; and
  a locking member configured to prevent movement of the manipulation member with respect to the stationary member at one or more different positions along the slot, between a proximal end abutment and a distal end abutment of the slot of the stationary member.

2. The triphalangeal stabilization feature according to claim 1, wherein the stationary member is releasably coupled to the ultrasound probe.

3. The triphalangeal stabilization feature according to claim 2, wherein the stationary member is coupled to the ultrasound probe via a threaded engagement, a clip and detent, an adhesive, a magnetic interaction, an interference fit, a press-fit, or a snap-fit engagement.

4. The triphalangeal stabilization feature according to claim 2, wherein the stationary member is configured to be coupled to the ultrasound probe through a sheath positioned over the ultrasound probe.

5. The triphalangeal stabilization feature according to claim 1, wherein the locking member comprises a ball and detent mechanism.

6. The triphalangeal stabilization feature according to claim 1, wherein the manipulation member comprises a post extending orthogonally from the stationary member, the post including a post shaft with a first diameter and a post head with a second diameter larger than the first diameter.

7. The triphalangeal stabilization feature according to claim 1, wherein the stationary member surrounds a distal end of the ultrasound probe in an interference fit.

8. The triphalangeal stabilization feature according to claim 7, wherein the stationary member comprises an aperture shaped and positioned to align with a lens of the ultrasound probe.

9. The triphalangeal stabilization feature according to claim 8, wherein the stationary member comprises a gel pad disposed over the aperture.

10. The triphalangeal stabilization feature according to claim 1, wherein the stationary member includes a needle guide.

11. The triphalangeal stabilization feature according to claim 1, wherein the manipulation member comprises a first post and a second post separated from the first post.

* * * * *